United States Patent
Polan et al.

(10) Patent No.: US 6,420,119 B1
(45) Date of Patent: Jul. 16, 2002

(54) METHODS OF DIAGNOSING AND TREATING URINARY INCONTINENCE RELATING TO COLLAGEN PROTEOLYSIS IN PELVIC SUPPORTING TISSUE

(75) Inventors: Mary Lake Polan, Palo Alto; Bertha Chen, Menlo Park, both of CA (US)

(73) Assignee: The Board of Trustees of the Leland Stanford Jr. University, Palo Alto, CA (US)

( * ) Notice: Subject to any disclaimer, the term of this patent is extended or adjusted under 35 U.S.C. 154(b) by 0 days.

(21) Appl. No.: 09/689,291

(22) Filed: Oct. 11, 2000

Related U.S. Application Data

(60) Provisional application No. 60/158,923, filed on Oct. 12, 1999.

(51) Int. Cl.[7] .......................... C12Q 1/68; C12P 19/34; G01N 33/53; A61K 38/00
(52) U.S. Cl. .......................... 435/6; 435/7.1; 435/91.2; 514/2
(58) Field of Search .......................... 514/2; 435/6, 7.1, 435/91.2, 810

(56) References Cited

U.S. PATENT DOCUMENTS

| | | | |
|---|---|---|---|
| 5,385,561 A | * 1/1995 | Cerny | 604/264 |
| 5,712,252 A | 1/1998 | Smith | 514/21 |
| 5,883,241 A | 3/1999 | Docherty et al. | 536/23.2 |
| 5,990,293 A | 11/1999 | Docherty et al. | 536/23.1 |
| 6,127,427 A | 10/2000 | Martin et al. | 514/740 |

OTHER PUBLICATIONS

Chen et al., Abstract submitted for the 20th Annual Scientific Meeting of the American Urogynecologic Society, Oct. 14–16, 1999.*

PCT International Search Report for PCT/US00/28105, filed Oct. 11, 2000.

Ulmsten, Ulf et al., "Different Biochemical Composition of Connective Tissue in Continent and Stress Incontinent Women," *Acta Obstet Gynecol Scand*, vol. 66, pp. 455–457 (1987).

Edwards, Dr. et al., "The roles of tissue inhibitors of metalloproteinases in tissue remodeling and cell growth," *International Journal of Obesity*, vol. 20, Suppl. 3, pp. 9–15 (1996).

Bergman, Arieh, et al., "Biochemical Composition of Collagen in Continent and Stress Urinary Incontinent Women," *Cynecol Obstet Invest*, vol. 37, pp. 48–51 (1994).

Jackson, S.R., et al., "Changes in metabolism of collagen in genitourinary prolapse," *The Lancet*, vol. 347, pp. 1658–1661 (1996).

Falconer, Christian et al., "Decreased Collagen Synthesis in Stress–Incontinent Women," *Obstetrics & Gynecology*, vol. 84, No. 4, Part 1, pp. 583–586 (Oct.1994).

Falconer, Christian et al., "Paraurethral connective tissue in stress–incontinent women after menopause," *Acta Obstet Gynecol Scand*, vol. 77, pp. 95–100 (1998).

Falconer, Christian et al., "Different organization of collagen fibrils in stress–incontinent women of fertile age," *Acta Obstet Gynecol Scand*, vol. 77, pp. 87–94 (1994).

Versi, Eboo et al., "Correlation of urethral physiology and skin collagen in postmenopausal women," *British Journal of Obstetrics and Gynocology*, vol. 95, pp. 147–152 (Feb. 1988).

Sato, Takashi et al., "Hormonal regulation of collagenolysis in uterine cervical fibroblasts," *Biochem. J.*, vol. 275, pp. 645–650 (1991).

Rajabi, Mohammad et al., "Hormonal Regulation of Interstitial Collagenase in the Uterine Cervi of the Pregnant Guinea Pig," *Endocrinology*, vol. 128, No. 2 (1991).

Raga, Francisco et al., "Independent Regulaton of Matrix Metalloproteinase–9, Tissue Inyhibitor of Metalloproteinase–1 (TIMP–1), and TIMP–3 in Human Endometrial Stromal Cells by Gonadotropin–Releasing Hormone: Implications in Early Human Implantation," *Journal of Clinical Endocrinology and Metabolism*, vol. 84, No. 2, pp. 636–642 (1999).

Bhatia, Narender N. MD, et al., "Effects of estrogen on urethral function in women with urinary incontinence," *Am. J. Obstet. Gynecol*, vol. 160, No. 1, pp. 176–181 (Jan. 1989).

Huang, Hong–Yuan et al., Cytokin–Mediated regulation of 92–Kilo9dalton Type IV Collagenase, Tissue Inhibitor of Metalloproteinase–1 (TIMP–1), and TIMP–3 Messenger Ribonuclic Acid Expression in Human Endometrial Stromal Cells, *Journal of Clinical Endocrinology and Metabolism*, vol. 83, No. 5, pp. 1721–1729 (1998).

Onisto, Maurizio et al., "Gelatinase A/TIMP–2 Imbalance in Lymph–Node–Positive Breast Carcinomas, as Measured by RT–PCR," *Int. J. Cancer*, vol. 63, pp. 621–626 (1995).

Dou, Qingchaun et al., "Differential expression of matrix metalloproteinases and their tissue inhibitors in leiomyomata: a mechanism for gonadotrophin releasing hormone agonist–induced tumour regression," *MolecularHuman Reproduction*, vol. 5, No. 11, pp. 1005–1014 (1997).

\* cited by examiner

*Primary Examiner*—Kenneth R. Horlick
(74) *Attorney, Agent, or Firm*—Susan J. Friedman; Ann W. Speckman

(57) ABSTRACT

Methods are disclosed for diagnosing urinary incontinence or a predisposition to urinary incontinence in a subject by determining the ratio of expression levels of MMPs/TIMPs in pelvic supporting tissue of the subject and comparing the ratio to a predetermined indicator. A diagnostic kit is also disclosed. Methods are disclosed for treating urinary incontinence by reducing proteolysis of collagen in pelvic supporting tissue of the subject and for identifying therapeutic agents in in vitro screens.

12 Claims, 6 Drawing Sheets

METHODS OF DIAGNOSING AND TREATING URINARY INCONTINENCE RELATING TO COLLAGEN PROTEOLYSIS IN PELVIC SUPPORTING TISSUE

CROSS-REFERENCE TO PRIOR APPLICATIONS

This application claims the benefit of priority to U.S. Provisional application No. 60/158,923, filed Oct. 12, 1999.

BACKGROUND

1. Field of the Invention

This invention relates to novel methods for diagnosing, preventing or delaying the onset of, and treating urinary incontinence. The methods involve detecting and modulating the proteolysis of collagen in pelvic supporting tissue. More particularly, the methods of this invention relate to the differential expression of the matrix metalloproteinases (MMPs) known to degrade extracellular matrix collagen and the tissue inhibitors of metalloproteinases (TIMPs) which specifically inhibit MMP proteolytic activity. The invention also relates to a novel method of screening for specific modulators and inhibitors of pelvic collagen degradation.

2. State of the Art

Urinary incontinence and pelvic floor dysfunction are a major public health problem in the United States. A decade ago the National Institutes of Health estimated that at least 10 million American adults suffered from urinary incontinence (1). In addition, two-thirds of the burden of urinary incontinence is borne by women with prevalence rates ranging from 14% to 41% depending on the study population definition. Currently, American women can expect a 11.1% lifetime risk of undergoing surgery for incontinence or pelvic organ prolapse by the age of 80 and of those who do undergo surgery, close to 30% will require a repeat operation for recurrent urinary dysfunction (2), thus defining a growing area of disability for women for which no medical prophylaxis or therapy currently exists.

1. Collagen Content and Expression.

Collagen is composed of three polypeptide chains assembled in a triple helix, which is then supercoiled (3). Collagen forms the matrix of connective tissue and is made through very complex post-translational processing which ultimately requires crosslinking of the fascial collagen chains by pyridinoline in order to mature into a high tensile strength support structure (4). Over a dozen types of collagen have been identified, with types I and III being the main structural components of epithelial tissue (5), vaginal epithelium, and endopelvic fascia (6). Type I collagen is most abundant in the skin, tendons, ligaments, bones, and cornea where it comprises over 80% of the total collagen. Type II collagen is primarily present in cartilage, and type III collagen has the same distribution as does type I, but the ratio between the two varies. Type III collagen appears to be more abundant in the dermis during early fetal development and is thought to contribute to the elastic properties of the tissue (5).

Mechanical stability of the genito-urinary tract depends on intact, functional collagen fibers, which support the bladder neck, urethra, and pelvic organs. There are several reports in the literature that suggest that women with stress urinary incontinence, and perhaps those with prolapse as well (7), have lower levels of total collagen in vesicovaginal fascia (8), abdominal skin, and round ligament (9) than control, continent women. Collagenous tissue from the vaginal wall is representative of tissue from the uterosacral and round ligaments (7) as well as tissue supporting the urethra, bladder, and bladder base (6). The content of type III collagen in perineal skin, uterosacral ligaments, and round ligaments of women with stress urinary incontinence was shown to be significantly reduced compared to that of women without SUI (6). In addition, there was a positive correlation between urethral pressure measurements and collagen content in abdominal skin as measured by hydroxyproline (10). Consistent with these in vivo observations, an in vitro study of fibroblasts cultured from skin biopsies of women with stress incontinence showed a 30% decrease in collagen accumulation compared to cultures from continent women (11).

Other studies have compared mRNA levels for specific collagen types (12), the pyridinoline crosslink content of collagen (13,14), collagen fiber size by transmission electron microscopy (12), ratios of type I/type III collagens (14), levels of type I collagen (15). However, such studies have yielded conflicting and/or inconclusive results.

2. Collagen Metabolism

Collagen is a metabolically active structure with constant turnover mediated through proteolysis by a group of enzymes termed matrix metalloproteinases (MMPs) and their specific inhibitors, tissue inhibitors of matrix metalloproteinase (TIMPs).

Matrix metalloproteinases (MMPs) are a family of structurally related proteins which degrade extracellular matrix and basement membrane components (16). They are produced as proenzymes and activated through proteolytic cleavage by other MMPs or plasmin. Interstitial collagens (types I, II, and III), the most abundant connective tissue proteins, are cleaved by the interstitial collagenases (MMP-1, MMP-8, and MMP-13) which specifically cleave native triple helical collagen at a single peptide bond in each a chain, yielding two fragments (17). This single site for cleavage ($Gly_{775}$-$Leu/Ile_{776}$) produces both three-quarter ($TC^A$) and one-quarter ($TC^B$) length collagen fragments (18) generating two neoepitopes: ($COL2$-$3/4C_{short}$) on the carboxy-terminal end and COL2-1/4N1 on the amino-terminus. Specific antibodies to these carboxy- and amino-terminal neoepitopes have been utilized to document increased collagenase activity in cartilage from patients with osteoarthritis compared to nonarthritic cartilage (19) and excessive collagenase activity in human atheromatous plaques (20).

These one-quarter and three-quarter length collagen fragments are very susceptible to rapid gelatinase (MMP-2 and MMP-9) degradation to amino acids (21). Importantly, MMP-2 may also act on intact collagen degrading it to quarter length fragments similarly to MMP-1 (17). Thus, the interstitial collagenases and the gelatinases together are capable of completely degrading intact collagen fibers. As such, MMP-2 and MMP-9 may be critically important to loss of strength of fibrous collagen and, ultimately, with sufficient degradation, to loss of tissue strength.

In the extracellular matrix, the activity of MMPs is tightly regulated by a family of natural inhibitors, the tissue inhibitors of metalloproteinase (TIMPs). TIMP-1, TIMP-2, TIMP-3, and TIMP-4 have been described (22). TIMP-1 is a glycoprotein of molecular weight 28.5 kDa which binds stoichiometrically with MMP-9. TIMP-2 is a 21 kDa protein which binds to MMP-2. TIMP-3, a novel member of the TIMP family, has inhibitory activity against MMP-9 as well as stromelysin-1 and MMP-1. TIMP-3 is the only member of the TIMP family which is found exclusively in the extracellular matrix and it appears to be the most effective inhibitor of MMP-9 (23). The most recently discovered TIMP-4 appears primarily in cardiac tissue and may function to maintain extracellular matrix hemostasis (22). A single study addressed MMP levels and has shown significant increases in MMP-2 and MMP-9 in pelvic tissue from premenopausal women with prolapse, but not incontinence, when compared with normal women (7), implying increased metabolic turnover, and decreased mechanical strength in the tissue. There is no information about TIMP expression in pelvic tissue in incontinent women.

The MMP-2/TIMP-2 ratio has been found to correlate with the invasiveness of breast carcinomas, suggesting the potential utility of this ratio as an early prognostic tool to determine more reliably the aggressiveness of the breast cancer (24).

3. Modulators of MMP and/or TIMP Expression.

(a) GnRH Agonist: Trophoblast invasion is regulated in part by MMP-9 which can be inhibited by both TIMP-1 and TIMP-3 (25). We have shown that TIMP-1 and TIMP-3 mRNA expression in cultured human endometrial stromal cells and protein secretion into the medium were significantly decreased by GnRH agonist when compared to control cells. Moreover, the expression of TIMP-1 appeared to be affected to a much greater extent than that of TIMP-3 (26).

(b) Cytokines and Growth Factors: The cytokine IL-1$\beta$ has also been shown to stimulate a two-fold increase in procollagenase production in pregnant Guinea pig cervix (27). Our laboratory has examined the ability of IL-1$\beta$ and transforming growth factor-$\beta$ (TGF-13) to regulate MMP-9, TIMP-1, and TIMP-3 mRNA expression in cultured human endometrial stromal cells (28). In these cultured endometrial stromal cells, TIMP-1 and TIMP-3 but not MMP-9 mRNA were expressed. However, incubation with IL-1$\beta$ resulted in stimulation of MMP-9 expression and a decrease in both TIMP-1 and TIMP-3 mRNA expression in a dose-dependent maimer. Conversely, TGF-$\beta$ augmented TIMP-1 and TIMP-3 mRNA expression suggesting that IL-1$\beta$ and TGF-$\beta$ may play opposing roles at the embryo-maternal interface during trophoblast invasion by regulating stromal cell expression of both TIMPs and MMP-9 (28).

(c) Gonadal Steroids: Gonadal steroids have been shown both in vivo and in vitro to affect collagen status in women with SUI. Physiologically, estrogen has been shown to increase urethral pressure in postmenopausal women (29). In addition, approximately 50% of women with SUI reported subjective improvement in symptoms after estrogen treatment. For example, 6 of 11 patients who were given vaginal estrogen creme daily for 6 weeks were cured or improved significantly with that therapy (29). On the other hand, other studies have suggested that hypoestrogenism may simply affect the sensory threshold of the lower urinary tract, resulting in incontinence through a neural mechanism (30). Conflicting in vivo evidence suggests that mixed groups of pre- and postmenopausal women with SUI have a lower content of pelvic collagen than controls (6, 8, 9, 11), but estrogen-replaced postmenopausal women do not (15). There is no information on the effect of estrogens, in vitro, on collagen synthesis in fibroblast cultures from incontinent women.

In vitro studies of collagen metabolism as a function of gonadal steroids have primarily been performed in animal models. For example, in the pregnant guinea pig cervix, procollagenase activity doubled in the presence of 17$\beta$-estradiol and estrone (27) while in cultured rabbit uterine cervical fibroblasts, treated with progesterone or 17$\beta$-estradiol, levels of procollagenase in the culture medium declined (31). However, under the same conditions, the level of TIMPs in the culture media increased as a function of incubation with progesterone and 17$\beta$-estradiol. The suppression of MMP production and increase in TIMP production by both steroids suggests that collagenolysis in rabbit uterine cervical fibroblasts is negatively regulated by steroid hormones which modulate the ratio of MMP/TIMP at a pretranslational level (31). In human endometrium, gene expression of matrix metalloproteinases during the menstrual cycle is repressed by progesterone which was confirmed by immunoprecipitation of MMPs in explant cultures (32). In other experiments with human fibroblast cultures (11, 33), the effect of gonadal steroids was not examined. However, confirmation of estrogen receptors (8, 34) and progesterone receptors (34) in female pelvic floor tissue is consistent with a gonadal steroid-mediated response and provides a rationale for estrogen treatment of women with uro-genital disorders (29).

A single report on androgens confirms the ability of intravenous dehydroepiandosterone sulfate (DHEAS), a weak androgen, to increase collagenase activity in the human cervix by over 150% (35). This experiment on human cervix was performed to determine the ability of DHEAS to induce cervical ripening but also suggests that there are androgen receptors in the human cervix which may be involved in modulation of collagenase activity 4. Reversal of Collagenolysis by TIMP Inhibitors Excessive collagenolysis mediated by MMPs appears to accelerate human disease processes such as tumor invasion, joint destruction in arthritis, and vascular aneurysm formation. Several studies have examined the ability of MMP inhibitors to reverse these pathologies. For example, BB-94 (Batimastat), a specific inhibitor of MMPs, was evaluated for its ability to control aneurysm growth in rat aorta. Rats treated with this inhibitor showed significantly less aneurysmal dilatation than did control rats (36). Others have shown that synthetic, pharmaceutically developed metalloproteinase inhibitors that mimic TIMP-2 but not TIMP-1 activity can inhibit shedding of TNF-$\alpha$ receptors in the human colon adenocarcinoma cell line (37). One of these drugs, Marimastat, has been used in a Phase I study to evaluate treatment of inpatients with advanced lung carcinoma. Marimastat was found to be well absorbed from the GI tract reaching plasma levels substantially higher than those required for MMP inhibition in vitro (38). Other MMP inhibitors have been developed and tested as potential therapeutic agents in the treatment of abdominal aortic aneurysm For example, RS 132,908, promoted preservation of aortic elastin and an enhanced fibrotic response within the aortic wall in male rats (39). RS 113,456 has been shown in vivo in male rats to diminish flow mediated arterial enlargement through MMP inhibition. This drug inhibits MMP-2 and MMP-9 with a $K_I$ in the human of 0.054 and 0.065 (nmol/L), respectively, thus providing an order of magnitude greater inhibition of MMP-2 and MMP-9 than for other MMPs (40).

In view of the high prevalence rates of urinary incontinence among older women, and the absence of a medical therapy for this disorder, there is a continuing need for methods that are capable of detecting predisposition to development of urinary dysfunction leading to stress urinary incontinence in women. As well, there is a need for methods of screening for therapeutic agents that are capable of reversing the pathophysiologic changes that appear to be associated with collagen degradation in pelvic tissue of women as they age.

SUMMARY OF THE INVENTION

The present invention satisfies the above needs by providing methods for diagnosing and treating urinary incontinence by detecting and reducing proteolysis of collagen in pelvic supporting tissue. The diagnostic methods are useful in detecting predisposition to development of urinary incontinence such that prophylactic treatment can be initiated to prevent the onset of symptoms.

One preferred embodiment of the invention is a method that sensitively reflects variations in collagen turnover in pelvic support tissue and can be used to detect predisposition to development of urinary incontinence and other conditions that are related to the weakening of mechanical stability of support tissues of the genitourinary tract (e.g., conditions resulting from genetic predisposition, hormonal imbalance, trauma and others). Another preferred embodiment is a method for diagnosing urinary incontinence in a subject based on a determination of the rate or degree of proteolysis of collagen in pelvic supporting tissue. The method is based on the inventors' experimental findings that expression levels of MMPs and/or TIMPs are outside "normal" ranges, and that MMP/TIMP expression ratios are elevated in pelvic supporting tissue of women with urinary incontinence, as compared to women with normal urinary function.

According to one embodiment, methods of the present invention involve determining the level of at least one MMP in pelvic supporting tissue in the subject, determining the level of at least one TIMP in pelvic supporting tissue in the subject; calculating a ratio of MMP/TIMP levels in the subject; and comparing the ratio to a predetermined indicator. The predetermined indicator is typically based on statistical assessment of MMP/TIMP expression ratios obtained from subjects with normal urinary function and subjects with actual or incipient urinary incontinence. Ratios can be determined from quantitative measurements of mRNA and protein levels or activities.

According to another embodiment, methods of the present invention involve determining collagen degradation and/or content in pelvic supporting tissue in a subject and comparing the collagen degradation and/or content to a predetermined indicator. Preferably, collagen degradation assays will measure the amount of initial cleavage products of collagen breakdown by MMPs (e.g., the carboxy-terminal neoepitope COL2-3/4 $C_{short}$).

In another embodiment, the MMP/TIMP ratio method is used to determine whether a patient may benefit by treatment with one or more agents for modulating the expression or activity of MMPs and TIMPs (e.g., gonadal steroids, cytokines, growth factors, MMP inhibitors, TIMP analogs or derivatives) and/or collagenases.

The present invention also provides a diagnostic kit for assessing whether levels or activities of MMPs and TIMPs in a biological sample from an individual with symptoms of urinary incontinence are abnormal. The biological sample may be a bodily fluid, a cell or tissue sample or an extract or lysate thereof, or a cultured tissue. In one embodiment, the kit comprises a test for the activity or level of one or more MMPs, a test for the level of one or more TIMPs in the sample, and a predetermined indicator of normal and abnormal values for the tests. The predetermined indicator is an empirically determined value or range of values that is typically determined from test measurements on groups of normal subjects and subjects with urinary incontinence (or a predisposition for urinary incontinence). The test may be quantitative, e.g., for use in a clinical laboratory setting, or qualitative (e.g., detecting TIMP or MMP only when present in the sample at a certain predetermined cut-off level), e.g., for home use. Positive and negative controls may also be included in the kit. In another embodiment, the kit comprises a test for collagenase activity. Various technologies for home testing can be used in the practice of this embodiment. For example, tests are available that utilize specific antibodies or enzyme substrates bound to a substratum for detecting a protein level (or activity) or range of levels (or activities) in a predetermined volume of biological sample. The technologies that form the basis for these tests are well known to those skilled in clinical laboratory medicine. Any test that distinguishes between normal and abnormal levels can be used, provided that it is convenient to perform and is specific for measurement of the desired parameters.

Various procedures for quantitating protein levels, enzymatic activities and/or mRNAs are illustrated in the Examples below. Of course, it is recognized that other useful measurement techniques are well-known to biochemists, immunobiologists and molecular biologists, and can be substituted for the procedures described herein.

Screening assays for identifying therapeutic agents that modulate proteolysis of collagen in pelvic supporting tissue are also provided by the present invention. These assays may be carried out with cell-free preparations (e.g., cell extracts, isolated collagenases, MMPs, TIMPs), isolated tissues and cell preparations, or cultured cells. It is anticipated that for some purposes (e.g., screening of libraries of chemical compounds and biotherapeutics), a first-stage screen that uses cell-free preparations will be employed to identify putative therapeutic modulators. Following this, one or more second-stage cell-based screens can be used to assess efficacy.

In general, the screening assays are in vitro assays that employ pelvic support tissue explants, cultures of cells derived from pelvic support tissues, or cultures of well-characterized cells that simulate the aberrant collagen turnover of pelvic support tissues from subjects with urinary incontinence. The screening assays involve measuring the activity of MMPs, or the relative protein levels of MMPs and TIMPs in pelvic support tissues or cells before and after treatment with at least one candidate therapeutic agent, and comparing the before and after activities or protein levels.

In another embodiment, a candidate therapeutic agent is screened for its effect on collagen proteolysis in pelvic support tissue explants or cultured cells, e.g., by quantitating the carboxy-terminal neoepitope produced by collagen cleavage. This direct measurement of collagenase activity may be carried out in conjunction with measurements of activity of MMPs or relative protein level of MMPs and TIMPs, as described above, to identify agents that selectively modulate collagenase activity and agents that have multiple effects on collagen turnover.

Therapeutic agents discovered with the use of the screening assays disclosed herein are also intended to be within the scope of this invention.

The present invention also provides methods of treating urinary incontinence, preferably in a mammal, and most preferably in a human. These methods encompass both prophylactic therapy (i.e., preventing or delaying the onset of urinary incontinence in predisposed subjects), and treatment of actual urinary incontinence. Each of the therapies is directed to reducing or proteolysis of collagen in pelvic supporting tissue. Preferred methods for reducing proteolysis of collagen in pelvic supporting tissue include: modulatin at least one of the level and activity of MMPs in the pelvic supporting tissue; modulating at least one of the level and activity of TIMPs in pelvic supporting tissue; and administering an agent that reduces or inhibits proteolysis of collagen in pelvic supporting tissue (e.g., gonadal steroids, growth factors, cytokines, and combinations thereof, TIMPs, TIMP analogs or derivatives).

It is preferred that MMP modulators used for the treatment of urinary incontinence include modulators of MMP-1, MMP-2 and MMP-9 which are known to be involved in collagen breakdown in pelvic supporting tissue. These modulators may be naturally-occurring tissue inhibitors of MMP activity (e.g., TIMP-1, TIMP-2, TIMP-3, TIMP-4) and synthetic derivatives and analogs thereof. Examples of such inhibitors include Batimastat (British Biotechnology Ltd., see EP-A-276436, and reference 36 disclosed herein), Marimastat (38) and RS 113,456 (Roche). Many other specific MMP inhibitors have been developed by pharmaceutical companies, including collagenase inhibitors, and are described in the patent literature. See, e.g., U.S. Pat. No. 6,127,427 and other patents cited therein. Inhibitors have also been developed that are active against several different MMPs (e.g., GM6001 (Galardin). It is expected that other useful inhibitors of MMP activity, such as peptides and peptidomimetics, will be identified using the screening assays of this invention.

Presently preferred modulators of MMP and TIMP expression include gonadal steroids, growth factors, cytokines and combinations of these.

Oligonucleotides directed against the sense strands of MMPs and TIMPs (i.e., antisense molecules) may also be of use in modulating the expression levels of MMPs and TIMPs. The design and administration of such antisense oligonucleotides is well known in the art.

The therapeutic compounds of the invention are usually administered in the form of pharmaceutical compositions. This invention therefore provides pharmaceutical compositions which contain, as the active ingredient, one or more compounds that modulate the proteolysis of collagen in pelvic supporting tissues and one or more pharmaceutically acceptable excipients, carriers, diluents, permeation enhancers, solubilizers and adjuvants. One or more compounds may be administered alone or in combination with other therapeutic agents, carriers, adjuvants, permeation enhancers, and the like. The compounds may be formulated using conventional techniques such as those described in *Remington's Pharmaceutical Sciences*, Mace Publishing Co., Philadelphia, Pa. 17$^{th}$ Ed. (1985) and "*Modern Pharmaceutics*", Marcel Dekker, Inc. 3$^{rd}$ Ed. (G. S. Banker & C. T. Rhodes, Eds. Pharmaceutically acceptable salts of the active agents (e.g., acid addition salts) may be prepared using standard procedures known to those skilled in the art of synthetic organic chemistry and described, e.g., by J. March, *Advanced Organic Chemistry: Reactions, Mechanisms and Structure*, 4$^{th}$ Ed. (New York: Wiley-Interscience, 1992).

The compounds of the invention may be administered by any of the accepted modes of administration of agents having similar utilities and/or pharmacokinetics, for example, by oral, topical, or by parenteral routes (e.g., intradermal, intravenous, subcutaneous, intramuscular), intra-articular, intraspinal, epidural, rectal, vaginal, or transdermal/transmucosal routes. The most suitable route will depend on the nature and severity of the condition being treated. Oral delivery and sustained local delivery to pelvic supporting tissue are presently preferred routes for the compounds of this invention. In making the compositions of this invention, the active ingredient is customarily diluted by an excipient. Some examples of suitable excipients for oral formulations include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: permeation enhancers, pH regulators, buffers, lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Alternatively, the compounds of this invention, particularly antisense molecules, peptides and other biotherapeutic modulators of MMP and TIMP expression, may be solubilized and encapsulated (e.g., in a lipo some or a biodegradable polymer) (52).

For topical use, the compositions can be in the form of emulsions, creams, jelly, solutions, ointments containing, for example, up to 5% by weight of the active compound. For parenteral administration, the compositions can be in the form of sterile injectable solutions and sterile packaged powders.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations.

Another preferred formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., an ampoule).

The compounds of the present invention, or their pharmaceutically acceptable salts, are administered in a therapeutically effective amount. Typical dosage levels are in the range of about 0.1 mg to about 1,000 mg per day. A dosage in the range of about 0.01 to about 100 mg per kg of body weight per day is preferred. It will be understood, however, that the amount of the compound actually administered will be determined by a clinician of ordinary skill in the art, in the light of the relevant circumstances, including the condition to be treated, the chosen route of administration, the actual compound administered and its relative activity, the age, weight, and response of the individual patient, the severity of the patient's symptoms, and the like. The compounds of this invention are intended for medical use in humans and nonhuman mammals with analogous disorders and conditions.

DESCRIPTION OF THE PREFERRED EMBODIMENTS

It should be appreciated by those skilled in the art that while the experimental data is directed towards stress urinary incontinence ("SUI") in female subjects, the invention is intended to encompass urinary incontinence and accompanying conditions in both males and females which involves abnormal collagen metabolism causing increased collagen degradation in pelvic supporting tissues. The embodiments of the invention have utility in veterinary medicine as well as human medicine. The Examples below are intended to describe the experimental support for the invention, but not to limit the scope of the invention in any way.

Figure 1:
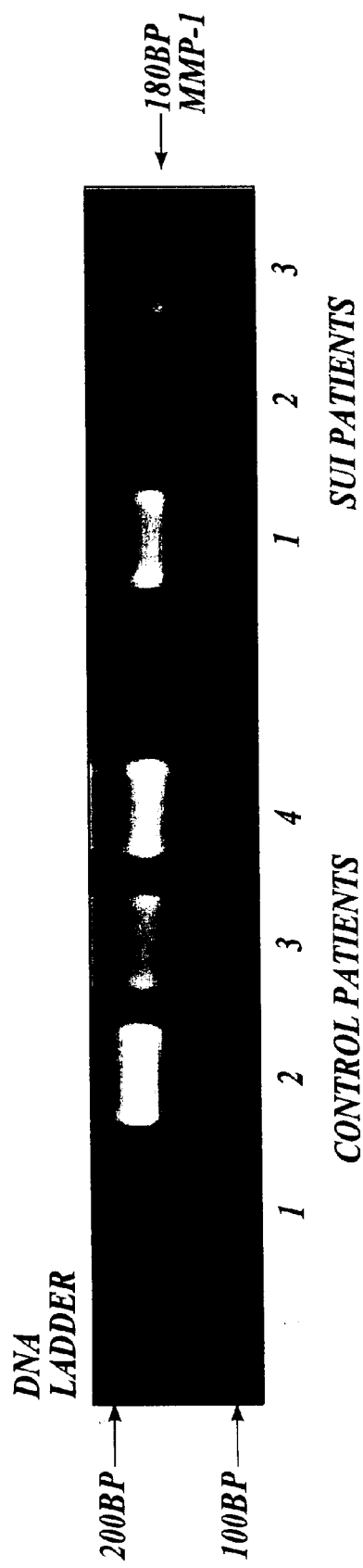
FIG. 1. MMP-1 mRNA expression in vaginal cuff tissue
Figure 2:
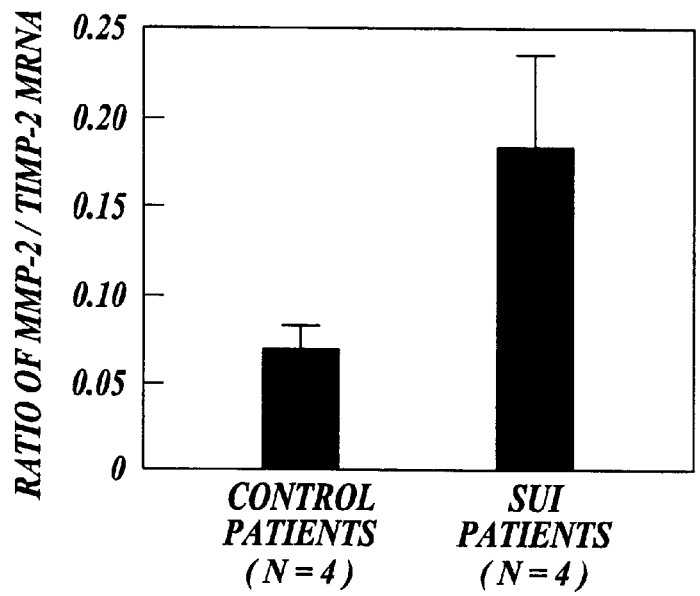
FIG. 2. Comparison of ratio of MMP-2/TIMP-2 mRNAs
Figure 3:
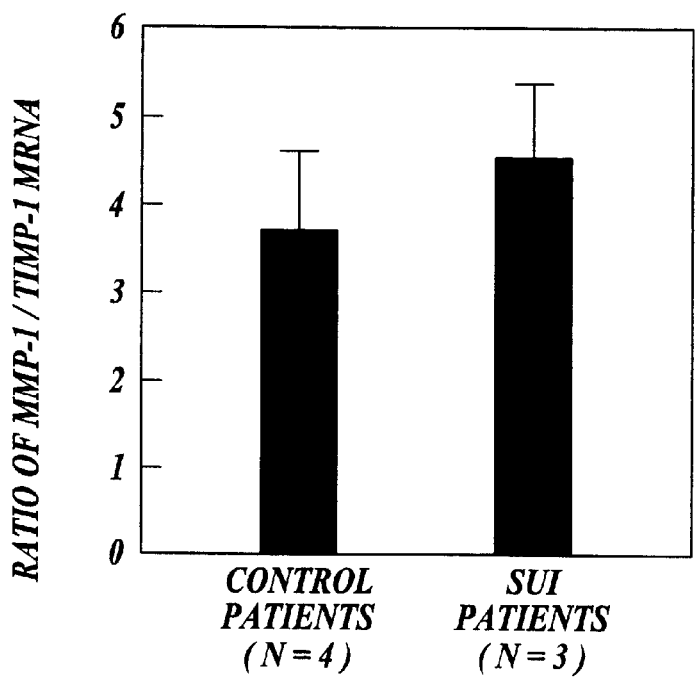
FIG. 3. Comparison of ratio of MMP-1/TIMP-1 mRNAs
Figure 4:
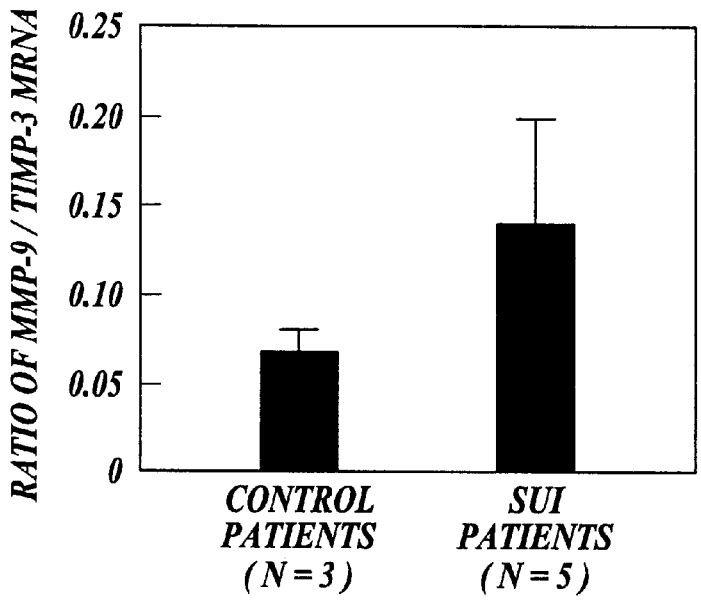
FIG. 4. Comparison of ratio of MMP-9/TIMP-3 mRNAs
Figure 5:
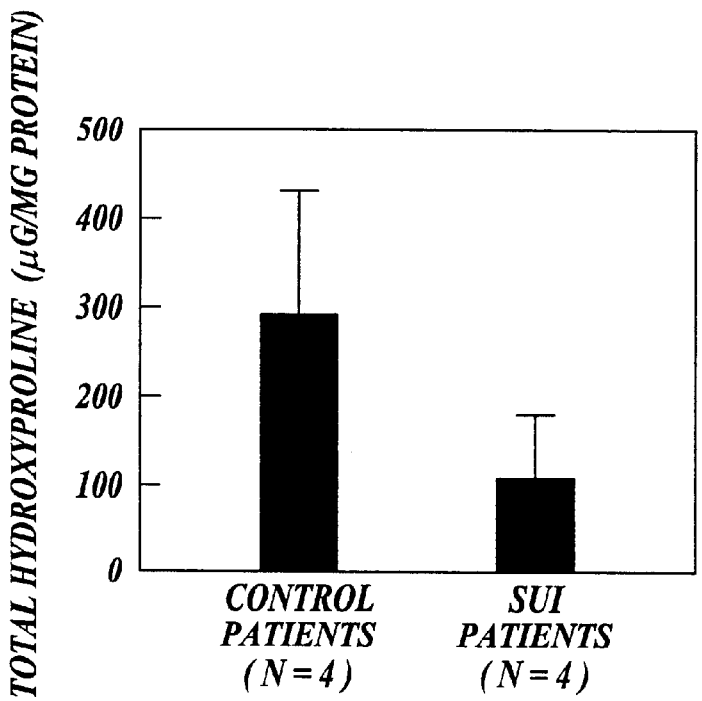
FIG. 5. Total collagen in vaginal cuff tissue
Figure 6:
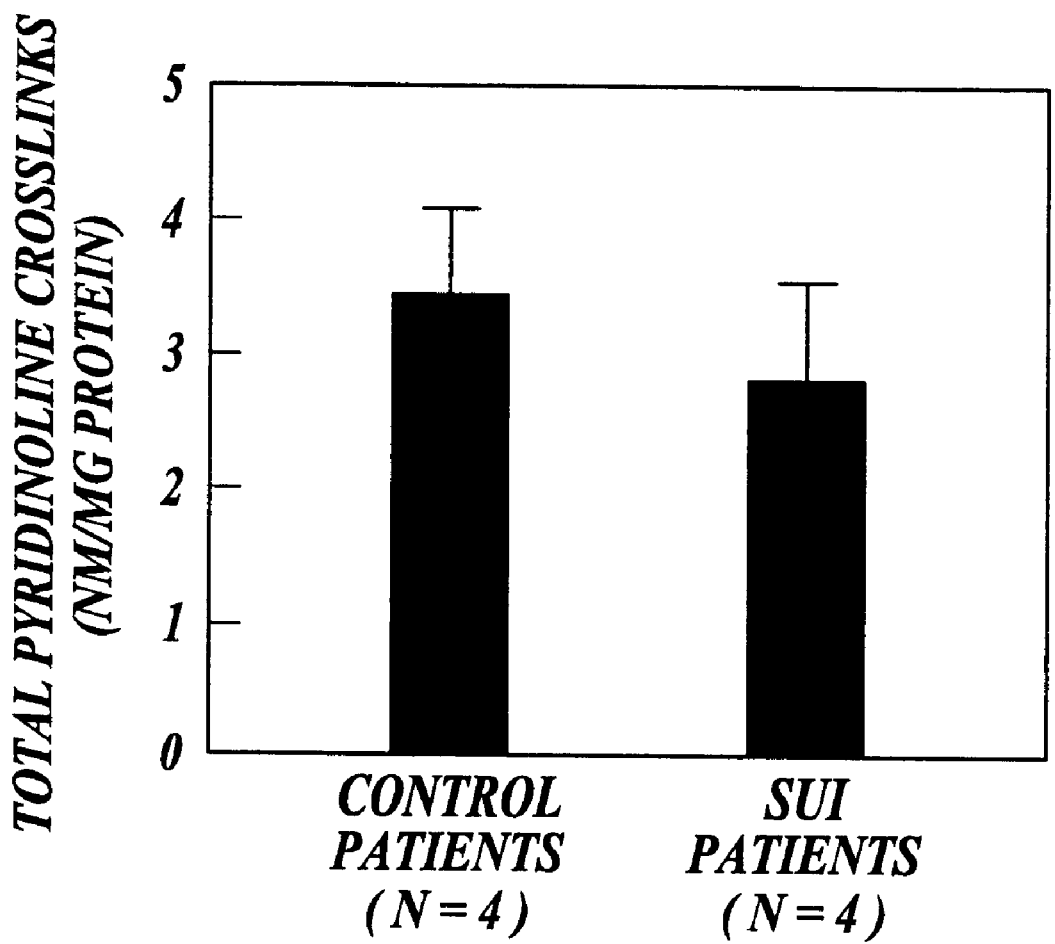
FIG. 6. Comparison of pyridinium crosslinks (Pyd and Dpd) in vaginal cuff tissue FIG. 7. Standard curve for MMP-9 quantitative PCR FIG. 8. Standard curve for TIMP-3 quantitative PCR

The methods of the present invention are based on the inventors' discovery that urinary incontinence in women is related to increased extracellular matrix proteolysis by matrix metalloproteinases. Experimental support for this discovery, and the methods disclosed herein, are explained in the experiments described below. The experiments were designed to identify the presence of MMP-1 mRNA in vaginal tissue from incontinent and control, continent women, and to measure quantitative mRNA expression of MMP-1, MMP-2 and MMP-9 and their inhibitors, TIMP-1, TIMP-2 and TIMP-3 (41, Appendix A). The gelatinases were examined because MMP-2 and MMP-9 in combination with MMP-1 degrade the major pelvic collagens completely to amino acids and are primarily inhibited by TIMP-2 and TIMP-3, respectively. The results from these experiments document the presence of MMP-1 mRNA in vaginal tissue from continent and incontinent women (FIG. 1) and show that the ratio of MMP-2/TIMP-2 mRNA expression is significantly ($p<0.04$) higher in women with stress urinary incontinence (SUI) compared to control women with no urinary dysfunction (FIG. 2). Other studies comparing the ratio of MMP-1/TIMP-1 and MMP-9/TIMP-3 mRNA expression also show higher ratios in women with SUI compared to control women (FIG. 3, FIG. 4). The MMP-1/TIMP-1 ratio has been found to be significantly higher ($p=0.04$) in the stress incontinent group compared to controls. In addition, the total collagen content of vaginal cuff tissue (FIG. 5) from women with SUI is lower when compared to normal women, as are pyridinium crosslinks (FIG. 6), consistent with an elevated MMP/TIMP ratio. These data suggest that women with SUI may have increased or abnormal collagen proteolysis resulting from increased expression of matrix metalloproteinases or decreased expression of TIMPs in pelvic tissue, and thus provide a a molecular pathophysiologic explanation for SUI.

EXAMPLES

1. Tissue Source

Vaginal cuff tissue was obtained from women undergoing hysterectomy and surgery for SUI. Tissue was obtained from the anterior vaginal cuff of three premenopausal women (ages 36–52) with normal estrogen levels and one postmenopausal woman (age 75) on a standard dose of hormone replacement therapy, so that all patients were estrogen-replete. Cuff tissue was taken from the anterior vaginal surface at the time of hysterectomy and placed immediately in ice cold PBS solution in the operating room to remove contaminating blood. After surgical removal of vaginal epithelium in the laboratory, tissue was processed immediately for RNA extraction. All women underwent urodynamic studies including a cystometrogram to confirm adequate bladder compliance and size as well as the absence of detrusor instability. All women had SUI secondary to hypermobility of the bladder neck. All women were evaluated on physical examination and found to have moderate to severe SUI of greater than one year duration requiring the daily wearing of pads with a positive cough stress test, leakage of urine, and moderate prolapse with vault desensus and a cystocele. All women were parous with 1 to 7 vaginal births. Women were treated with a variety of procedures including hysterectomy with anterior-posterior repair and pubovaginal sling, depending on the degree of stress incontinence. Control samples of anterior vaginal cuff tissue were taken from premenopausal women (ages 37–46) with normal estrogen levels undergoing hysterectomy for either dysfunctional bleeding or fibroids. Women with pelvic inflammatory disease, endometriosis, or malignant lesions were excluded from the study.

2. RNA Extraction

The extraction of RNA from the tissue samples was carried out with the RNA-STAT-60 reagent (Tel-Test Inc., Friendswood, Tex.) (28). Briefly, tissue samples were washed three times in PBS (Gibco BRL, Grand Island, N.Y.) to remove blood contamination. One hundred milligrams of tissue were homogenized in 1 ml of RNA-STAT-60 reagent. Total RNA was separated from DNA and proteins by adding chloroform and was precipitated using isopropanol. The precipitate was washed two times in 75% ethanol, air-dried, and rediluted in diethylpycocarbonate (DEPC)-treated $dH_2O$. Amount and purity of extracted RNA was quantitated by spectrophotometry in a GenQuant RNA/DNA calculator (Pharmacia Biotech Ltd., Cambridge, UK).

In order to measure the quantitative expression of MMP-1, MMP-2, MMP-9, TIMP-1, TIMP-2, and TIMP-3 mRNA, the technique of quantitative competitive reverse transcription polymerase chain reaction (QC-RT-PCR) was chosen. RT-PCR can be used to analyze low abundance mRNAs derived from cells or tissue and is a well established technique whose sensitivity provides a major advantage. Quantitative analysis of these messages can be achieved by a modification known as QC-PCR (40, 42), in which an internal control molecule possessing a small deletion in the amplified portion of the specific molecule is amplified simultaneously with the target sample instead of another control molecule such as β-actin or rRNA. Because the efficiency of the amplification of the internal control molecule is identical to that of the target template, quantitative PCR avoids discrepancies associated with tube-to-tube or sample-to-sample variations in the kinetics of the RT reaction (42, 43). As quantitative PCR is based on the competitive status between the target molecules and the internal standard molecules within the same PCR reaction, the relative amount of each product expressed is determined as a ratio of target to internal standard molecules. Differences as small as 20% between two samples can be determined with an accuracy of 95% (44).

3. Primers for Reverse Transcription (RT) and Polymerase Chain Reaction (PCR)

Specific sequences of oligonucleotide primers for MMP-9, TIMP-1, and TIMP-3 were obtained from Gene Bank Database of the National Center for Biotechnology Information (NCBI) of the National Institutes of Health (NIH, Internet address: http://www.ncbi.nlm.nih.gov). One corresponding set of primers for MMP-9, TIMP-1 and TIMP-3 was found with the help of the program OLIGO 5.0 Primer Analysis Software (National Bioscience, Plymouth, Minn.) and synthesized by the "Protein, Aminoacid and Nucleicacid (PAN)-Facility," Beckman Center, Stanford University, Stanford, Calif. Sequences for oligonucleotide primers for MMP-2 and TIMP-2 were obtained from the breast cancer literature (24). Primers for the interstitial collagenase MMP-1 were identified (45) and synthesized in the Beckman Center PAN-Facility. The human β-actin primers that were used to amplify an external standard were obtained from Clontech Laboratories, Inc., Palo Alto, Calif. β-actin mRNA expression was employed as an external positive control and was detected in all the samples studied, thus confirming the integrity of the RNA and the RT-PCR process.

4. RT

For RT-PCR, the Gen Amp RNA PCR kit (Perkin-Elmer, Foster City, Calif.) was used. Nineteen microliters of RT-mastermix for each sample were prepared containing 5 mmol/L $MgCl_2$, 1×PCR buffer II, 1 mmol/L of each deoxy-NTP, 2.5 μl/L oligo (deoxythymidine)$_{16}$, 20 IU ribonuclease inhibitor (all Perkin-Elmer), and 100 IU Moloney murine leukemia virus reverse transcriptase (Gibco BRL), and 1 μg total RNA diluted in 1 μl DEPC-treated $H_2O$ and filled into 0.5 ml thin wall PCR tube (Applied Scientific, South San Francisco, Calif.). RT-MasterMix in PCR tubes was covered with 50 μl of light white mineral oil and kept on ice until the RT. RT was carried out in the DNA Thermal Cycler 480 (Perkin-Elmer) using a program with the following parameters: 42° C., 15 min.; 99° C., 5 min.; then quenched at 4° C. After the reaction completed, samples were stored at −20° C. until the PCR. As negative control, 1 μL DEPC-treated $H_2O$ without RNA sample was subjected to the same RT reaction.

5. Construction of the Competitive- and Target-cDNA Fragments

A 440 base pair (bp), 473 bp, 590 bp, 969 bp fragment of native MMP-2, MMP-9, TIMP-2, and TIMP-3 cDNA (the target) (Table 1) was obtained by PCR amplification of reverse-transcribed total RNA from vaginal cuff samples with the regular 3' and 5' primers. The PCR product was visualized by agarose gel electrophoresis stained with ethidium bromide (ETB), and the cDNA was extracted from the gel, purified with an agarose gel extraction kit (Amersham Pharmacia Biotech Ltd., Arlington Heights, Ill.), and quantitated by spectrophotometry (Pharmacia Biotech Ltd., Cambridge, UK). To construct a competitive cDNA fragment: a floating primer with a sequence complementary to the cDNA between the 3' and 5' primer binding sites was designed by attaching the complementary sequence of the binding site of the original 3'-end MMP-2, MMP-9, TIMP-2, and TIMP-3 primer (Table 1). After PCR with the regular 5'-end primer and the 3'-end floating primer, the PCR product was visualized by agarose gel electrophoresis stained with ethidium bromide, cDNA extraction, purification and determination of the concentration performed as described above. This step resulted in cDNA fragments of MMP-2 (174 bp), MMP-9 (196 bp), TIMP-2 (227 bp), and TIMP-3 (464 bp). Primers for MMP-1 (Table 1) were identified to yield a 180 bp fragment on RT-PCR analysis.

TABLE 1

Structure of Target Primer Pairs and Competitive Primers for PCR Amplification

| Type of mRNA Oligonucleotide | | Size of Fragment | Stream | Sequence of Oligonucleotide (5'–3') |
|---|---|---|---|---|
| TIMP-1 | Target pair | 228 bp | 5'-end | TTCCACAGGTCCCACAACCGCAGC (SEQ ID NO: 1) |
| | | | 3'-end | CGT CCA CAA GCA ATG AGT (SEQ ID NO: 2) |
| | Competitive fragment | 124 bp | 3'-end | CGT CCA CAA GCA ATG AGT GGC TGT TCC AGG GA (SEQ ID NO: 3) |
| TIMP-2 | Target pair | 590 bp | 5'-end | TGC AGC TGC CCG GTG CAC (SEQ ID NO: 4) |
| | | | 3'-end | TTA TGG GTC CTC GAT GTC GAG (SEQ ID NO: 5) |
| | Competitive fragment | 227 bp | 3'-end | TTA TGG GTC CTC GAT GTC GAG GAG GAG GGG GCC GTG (SEQ ID NO: 6) |
| TIMP-3 | Target pair | 968 bp | 5'-end | TAC CAG AAA GAA TGA GGA ACC T (SEQ ID NO: 7) |
| | | | 3'-end | AGA GAG GGT GCT GAC GGT GTT (SEQ ID NO: 8) |
| | Competitive fragment | 464 bp | 3'-end | AGA GAG GGT GCT GAC GGT GTT CAG ACT CAG GAA CAT (SEQ ID NO: 9) |
| MMP-1 | Target pair | 180 bp | 5'-end | TCG GCC CCA AAG CAG CAG CTT C (SEQ ID NO: 10) |
| | | | 3'-end | CTT CAT GGT GTC TGC ATC AGC (SEQ ID NO: 11) |
| MMP-2 | Target pair | 440 bp | 5'-end | ACC TGG ATG CCG TCG TGG AC (SEQ ID NO: 12) |
| | | | 3'-end | TGT GGC AGC ACC AGG GCA GC (SEQ ID NO: 13) |
| | Competitive fragment | 174 bp | 3'-end | TGT GGC AGC ACC AGG GCA GCG TGG GAG CCA GGG CC (SEQ ID NO: 14) |
| MMP-9 | Target pair | 473 bp | 5'-end | GCC TGC CAC TTC CCC TTC ATC (SEQ ID NO: 15) |
| | | | 3'-end | CCC CAC TTC TTG TCG CTG TCA (SEQ ID NO: 16) |
| | Competitive fragment | 196 bp | 3-end | CCC CAC TTC TTG TCG CTG TCA GTT TCC CAT CAG (SEQ ID NO: 17) |

6. Standard Curve and Competitive PCR for MMP-1, MMP-2, MMP-9, TIMP-2, and TIMP-3

The standard curves for MMP-1, MMP-2, MMP-9, TIMP-2, and TIMP-3 were constructed by a coamplification of a constant amount of competitive cDNA with declining amounts of target cDNA obtained by serial dilution (28). Sixty microliters of the cDNA mix were added to 40 μl PCR-mastermixture containing 1.9 mM $MgCl_2$ solution, 10×PCR buffer II, 0.2 mM each dNTP, 2.5 U Taq-polymerase (all Perkin-Elmer), corresponding paired primers in a concentration of 0.2 μmol/L of each primer to a total volume of 100 μl and 14.5 μl DEPC-treated $H_2O$. The reaction was covered with 50 μl light white mineral oil and put in the Perkin-Elmer DNA Thermal Cycler 480. PCR cycles were composed of 1 cycle at 95° C. for 5 min. to denature all proteins, 30 cycles at 94° C. for 45 sec., at 55° C. for 45 sec., and at 72° C. for 60 sec. for MMP-9 and TIMP-3. PCR was performed in 35 cycles including 2 min.

denaturation at 94° C., 1 min. primer annealing at 56° C., and 2 min. extension at 72° C. for MMP-2 and TIMP-2. The reaction was terminated at 72° C. for 6 min. and was quenched at 4° C. PCR conditions for MMP-1 amplification were 30 cycles at 94° C. for 1 minute, 50° C. for 1 minute, and 72° C. for 3 minutes, followed by reaction termination at 72° C. for 6 minutes and quenching at 4° C.

Figure 7:
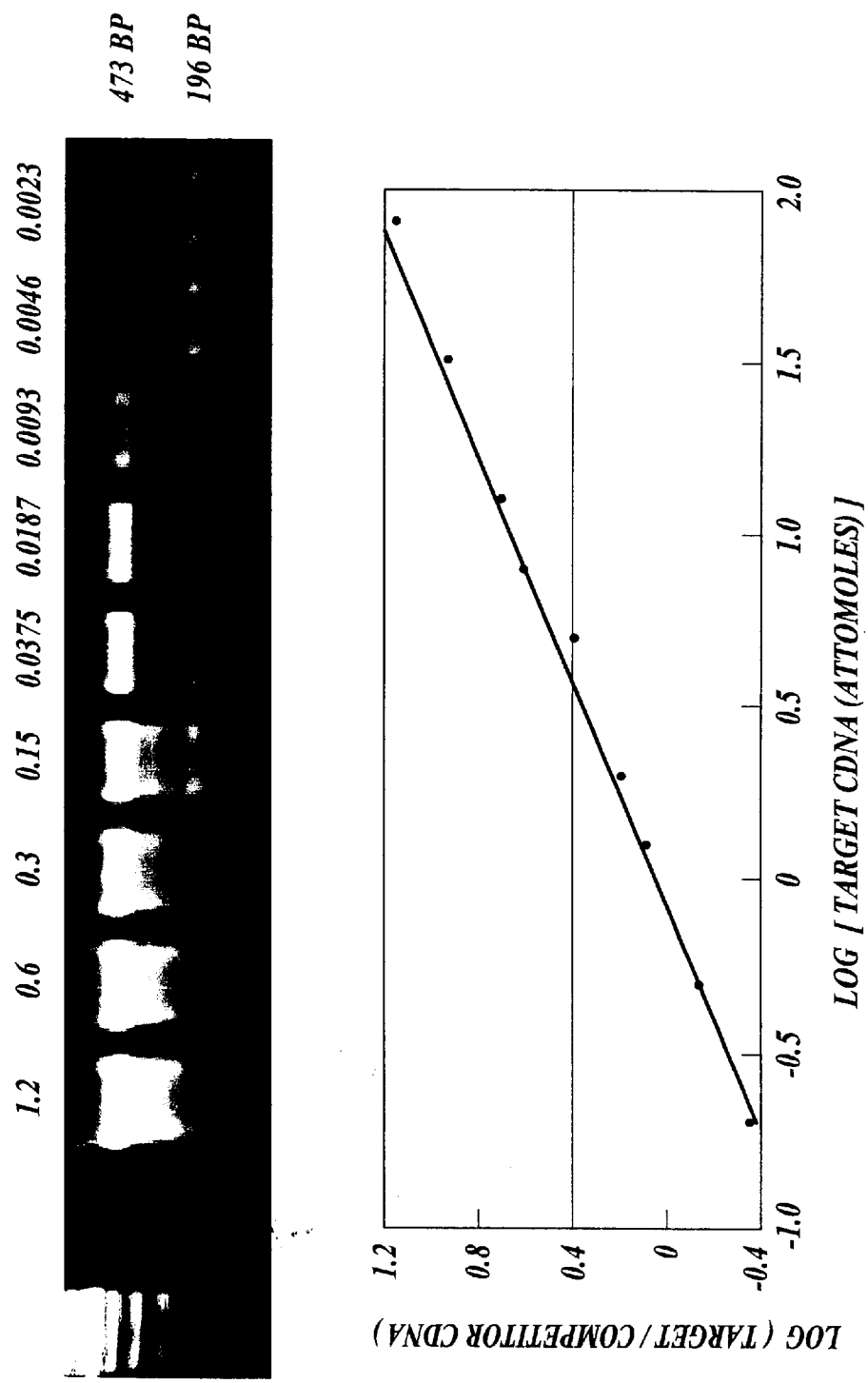
Figure 8:
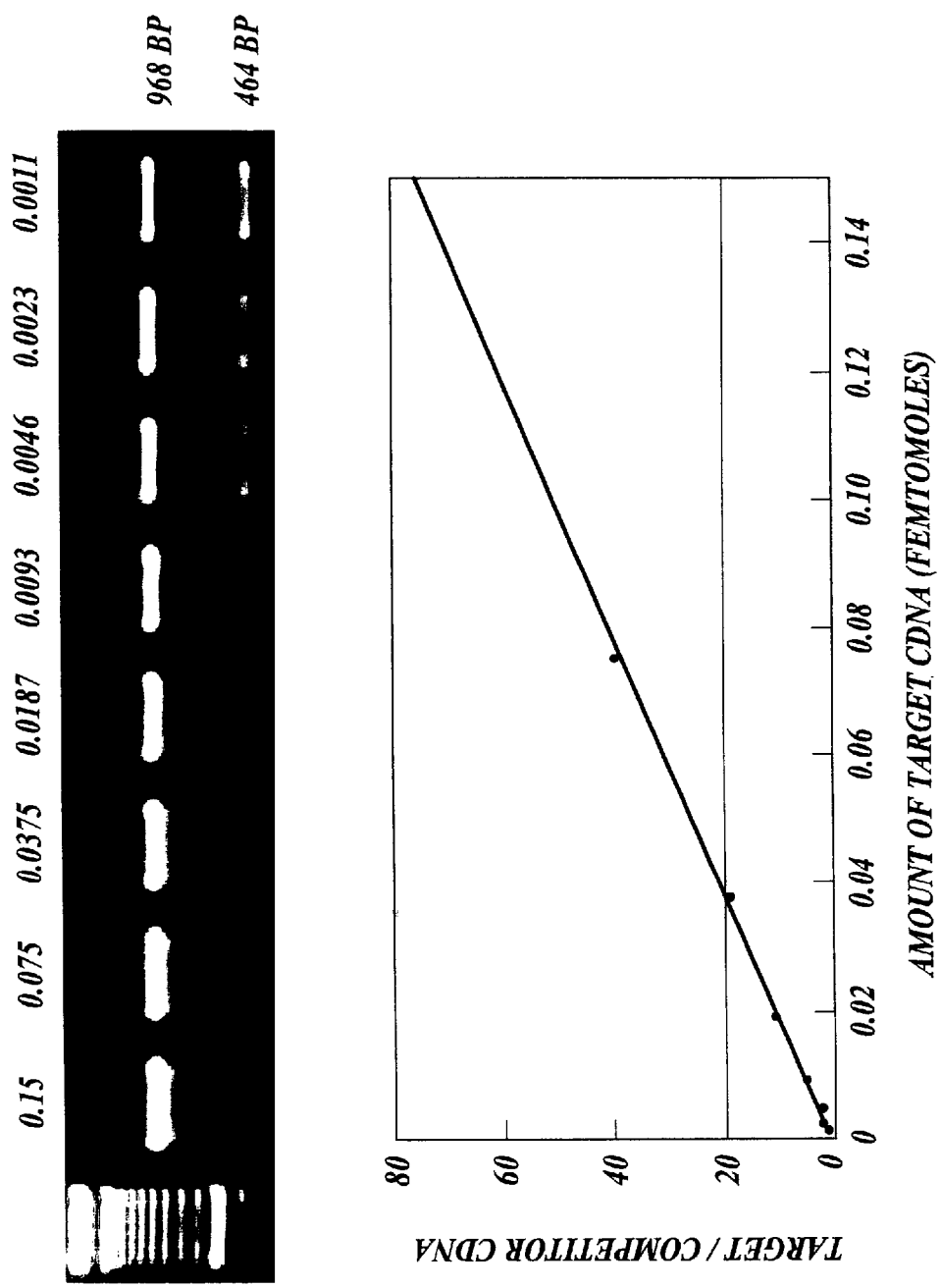

Two percent agarose gel (Life Technologies, Grand Island, N.Y.) electrophoresis was carried out in a H5 electrophoresis chamber. Gels were stained with ethidium bromide. Aliquots (25 μL) of each PCR product and dye buffer were analyzed in parallel with a 100-bp DNA ladder (Life Technologies, Grand Island, N.Y.) as a standard. After completion of electrophoresis, the gel blot was analyzed, and photocopies of the blot were printed by UV densitometry (Gel-Doc 1000 system, Bio-Rad Laboratories, Hercules, Calif.). The logarithmically transformed ratios of target cDNA to competitive cDNA were plotted against the log amount of initially added target cDNA in each PCR to obtain the standard curve. FIG. 7 and FIG. 8 show the standard curves for MMP-9 and TIMP-3 and are representative of the standard curves obtained for MMP-1, MMP-2 and TIMP-2. These standard curves were highly reproducible and linear. The values obtained from the regression line of the standard curves (y=b+mx) allowed us to calculate the amount of cDNA transcripts in an unknown sample. Therefore, competitive cDNA was added to each unknown sample before PCR. The ratio of the densities of sample target cDNA band to competitive cDNA were logarithmically transformed and compared to the values obtained from standard curve to quantitative mRNA expression in the experimental samples.

7. Fibroblast Cultures

Fibroblast cultures are started from biopsy specimens of vaginal tissue using an explant method (46). Ten small tissue samples of approximately 1 mm$^3$ are placed into 25 cm$^2$ of untreated plastic tissue culture flasks for primary explantation. After allowing tissue fragments to attach to the plastic surface for 15 minutes, 5 ml of culture medium consisting of 90% DMEM/10% fetal bovine serum, is added to the flasks. Cultures are incubated at 37° C. in an atmosphere of 95% air and 5% $CO_2$ and experiments performed on confluent cultures between passages 3 and 7 as described (46).

8. Tests of Putative Modulators (e.g., gonadal steroids, cytokines and growth factors)

Time course studies of both mRNA and protein expression in fibroblast cell cultures will determine an appropriate timeframe for these experiments which is expected to be 24 hours. Dose response studies are then performed as follows. Increasing concentrations of estrogen (0–10$^{-5}$M), progesterone (0–10$^{-5}$M), dihydro-testosterone (0–10$^{-5}$M), interleukin-1β (0–1,000 IU/ml), and TGF-β (0–40 ng/ml) are incubated with confluent human fibroblast cultures for 24 hours at 37° C. in an atmosphere of 95% air/5% $CO_2$. After 24 hours of incubation, supernatants are isolated and cells lysed by RNA-STAT 60. Both supernatants and cell lysates are examined for MMP-1, MMP-2, MMP-9, TIMP-1, TIMP-2, and TIMP-3 protein levels by ELISA (Oncogene Research, Cambridge, Mass.). Cells are harvested and RNA extracted as previously described (30). Quantitative mRNA expression of MMP-1, MMP-2, MMP-9, TIMP-1, TIMP-2, and TIMP-3 is measured using QC-RT-PCR. In experiments examining the ability of IL-β and TGF-β to modulate mRNA and protein expression of MMPs and TIMPs, appropriate anti-IL-1β and anti-TGF-β antibodies are employed to reverse the effect and thus confirm specificity of the response. The antiprogestin, RU-486, is used to reverse the effect of progesterone on MMP and TIMP expression, thus confirming specificity of the response.

9. Collagen Measurements

Vaginal cuff tissue is analyzed for collagen protein using a protease/acid methodology to determine hydroxyproline content for total collagen (47). Conditioned medium from fibroblast cultures and the cell monolayers themselves are both analyzed for hydroxyproline to determine total collagen content (47).

The specific antibodies for both type I and type III collagens are available (Accurate Chemical and Scientific Corp., Westbury, N.Y.) and are used to determine protein concentrations in vaginal cuff tissue and fibroblast cultures from control and incontinent patients using Western analysis (26, 48). Through a combination of QC-PCR and Western analysis, the ratio of type I/type III collagen in in vivo isolated vaginal cuff tissue and in vitro fibroblast cultures from control and incontinent patients is analyzed.

10. Pyridinoline Crosslinks

Vaginal cuff tissue is homogenized and treated with 6N HCl to degrade collagen and release pyridinoline crosslinks (49). Total Pyd and Dpd crosslinks is assayed by ELISA (Metra Biosystems, Mountain View, Calif., Appendix E) to determine the level of collagen crosslinking in tissue isolated from women with stress incontinence and control women. Supernatants from fibroblast cultures are collected and concentrated. Monolayer cultures are collected, treated with Triton X-100, and both supernatants and cell homogenates are assayed for pyridinoline crosslinks by ELISA (Metra Biosystems, Mountain View, Calif.).

11. Three-Quarter Length (Carboxy-Terminal) COL2-3/4$C_{short}$ Collagen Fragment Both the three-quarter ($TC^A$) and one-quarter ($TC^B$) length collagen fragments are a primary measure of initial collagen cleavage (18). Initial collagen cleavage of the triple helix generates a new carboxy-terminal end, COL2-3/4$C_{short}$ to which antibodies have been developed by Dr. Robin Poole. The level of the carboxy-terminal neoepitope is a direct measure of collagenase activity in osteoarthritic articular cartilage (18) and atheromatous plaques (23). In vaginal cuff tissue harvested from incontinent and control women, immunohistochemistry is used to assess the location and intensity of staining for the carboxy-terminal neoepitope as a measure of collagenolysis. In addition, total collagen is extracted and the level of the carboxy-terminal neoepitope is quantitated by ELISA.

Using cultured fibroblasts from vaginal wall tissue of continent and incontinent women, the level of carboxy-terminal neoepitope secreted into conditioned medium is determined using an ELISA (18). In addition, collagen is isolated from the cell fibroblast layer to determine intracellular neoepitope content.

12. Drug Screening

Fibroblast cultures from vaginal cuff tissue of premenopausal women with and without stress incontinence are established in untreated plastic dishes (46). Between passage 3 and 7, confluent cultures from each group of women are treated for an appropriate length of time with increasing concentrations of a putative therapeutic agent. (e.g., the Roche MMP inhibitor RS 113,456). A suitable dosage range for this inhibitor is 1 μg/ml–100 μg/ml in DMEM. Initial experiments are performed to determine the time course for inhibition of MMP activity by RS 113,456. After addition of RS 113,456 to fibroblast cultures, the earliest period at which steady state MMP inhibition is reached is identified. That time is subsequently used as a standard time of incubation for dose response curves. Cell supernatants are isolated and concentrated and fibroblast monolayers are homogenized using Triton X-100. To measure the specific proteolytic inhibition produced by RS 113,456, the MMP activities in supernatants and cell homogenates are examined by zymography with electrophoresis on premade gelatin gels (BioRad, Hercules, Calif.) (50,51). Using antibody which recognizes the COL2-3/4C$_{short}$ epitope (18), the level of collagenase activity is determined directly.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

REFERENCES CITED

1. Wall L L. Birth trauma and the pelvic floor: lessons from the developing world. J Women's Health 1999;8:149–154.
2. Olsen A L, Smith V J, Bergstom J O, Colling J C, Clark A L. Epidemiology of surgically managed pelvic organ prolapse and urinary incontinence. Obstet Gynecol 1997;89:501–506.
3. Van Der Best M, Garrone R. Collagen family of proteins. FASEB J 1991;5:2814–2823.
4. Eyre D R. The specificity of collagen cross-links as markers of bone and connective tissue degradation. Acta Orthop Scand 1995;66, Suppl 266:166–180.
5. Nimni M E. Collagen: Structure, function and metabolism in normal and fibrotic tissues. Seminars in Arthritis and Rheumatism 1983;13:1–86.
6. Bergman A, Elia G, Cheung D, Perelman N, Nimni M E. Biochemical composition of collagen in continent and stress urinary incontinent women. Gynecol Obstet Invest 1994;37:48–51.
7. Jackson S R, Avery N C, Tarlton J F, Eckford S D, Abrams P, Bailey A J. Changes in metabolism of collagen in genitourinary prolapse. The Lancet 1996;347:1658–1661.
8. Rechberger T, Donica H, Baranowski W, Jakowicki J. Female urinary stress incontinence in terms of connective tissue biochemistry. Europ J Obstet Gynecol and Reprod Biol 1993;49:187–191.
9. Ulmsten U, Ekman G, Giertz G, Malmström Different biochemical composition of connective tissue in continent and stress incontinent women. Acta Obstet Gynecol Scand 1987;66:455–457.
10. Versi E, Cardozo L, Brincat M, Cooper D, Montgomery J, Studd J. Correlation of urethral physiology and skin collagen in postmenopausal women. Brit J Obstet Gynaecol 1988;95:147–152.
11. Falconer C, Ekman G, Malmström A, Ulmsten U. Decreased collagen synthesis in stress-incontinent women. Obstet Gynecol 1994;84:583–586.
12. Falconer C, Blomgren B, Johansson O, Ulmsten U, Malmström A, Westergren-Thorsson G, Ekman-Ordeberg G. Different organization of collagen fibrils in stress-incontinent women of fertile age. Acta Obstet Gynecol Scand 1998;77:87–94.
13. Sayer T R, Dixon J S, Hosker G L, Warrell D W. A study of paraurethral connective tissue in women with stress incontinence of urine. Neurol Urodynam 1990;9:319–452.
14. Keane D P, Sims T J, Abrais P, Bailey A J. Analysis of collagen status in premenopausal nulliparous women with genuine stress incontinence. Br J Obstet Gynaecol 1997;104:994–998.
15. Falconer C, Ekman-Ordeberg G, Blomgren B, Johansson O, Ulmsten U, Westergren-Thorsson G, Malmstrom A. Paraurethral connective tissue in stress-incontinent women after menopause. Acta Obstet Gynecol Scand 1998;77:95–100.
16. Chung H W, Wen Y, Nezhat C, Woo B H, Polan M L. Matrix metalloproteinase-9 (MMP-9) and tissue inhibitor of metalloproteinase-3 (TIMP-3) m-RNA expression in endometriosis: MMP-9/TIMP-3 ratio in ectopic and eutopic endometrium. Submitted to Fertil Steril.
17. Aimes R T, Quiqley J P. Matrix metalloproteinase-2 is an interstitial collagenase. J Biological Chemistry 1995;270:5872–5876.
18. Billinghurst R C, Dahlberg L, Ionescu M, Reiner A, Bourne R, Rorabeck C, Mitchell P, Hambor J, Diekmanu O, Tschesche H, Chen J, Van Wart H, Poole A R. Enhanced cleavage of type II collagen by collagenases in osteoarthritic articular cartilage. J Clin Invest 1997;99:1534–1545.
19. Hulley S B, Cummings S R (eds). *Designing Clinical Research. An Epidemiologic Approach*. Baltimore: Williams & Wilkins, 1988.
20. Sukhova G K. Schönbeck U, Rabkin E, Schoen F J, Poole A R, Billinghurst R C, Libby P. Evidence for increased collagenolysis by interstitial collagenases-1 and -3 in vulnerable human atheromatous plaques. Circulation, submitted.
21. Wilhelm S M, Collier I E, Manner B L, Eisen A Z, Grant G A, Goldberg G I. SV40-transformed human lung fibroblasts secrete a 92-kDa type IV collagenase which is identical to that secreted by normal human macrophages. J Biol Chem 1989;264:17213–17221.
22. Gomez D E, Alonso D F, Yoshiji H, Thorgeirsson U P. Tissue inhibitors of metalloproteinases: structure, regulation and biological functions. Europ J Cell Biol 1997;74:111–122.
23. Edwards D R, Beaudry P P, Laing T D, Kowal V, Leco K J, Leco P A, Lim M S. The roles of tissue inhibitors of metalloproteinases in tissues remodelling and cell growth. Int J Obes Relat Metab Disord 1996;20:S9–15.
24. Onisto M, Riccio M P, Scannapieco P, Caenazzo C, Griggio L, Spina M, Stetler-Stevenson W G, Garbisa S. Gelatinase A/TIMP-2 imbalance in lymph-node-positive breast carcinomas, as measured by RT-PCR. Int J Cancer 1995;63:621–626.
25. Librach C L, Werb Z, Fitzgerald M L, Chiu K, Corwin N M, Esteves R A, Grobelny D, Galardy R, Damsky C H, Fisher S J. 92-kD type IV collagenase mediates invasion of human cytotrophoblasts. J Cell Biol 1991;113:437–449.
26. Raga F, Casañ E M, Wen Y, Huang H Y, Bonilla-Musoles F, Polan M L. Independent regulation of matrix metalloproteinase-9, tissue inhibitor of metalloproteinase-1 (TIMP-1), and TIMP-3 in human 27. Rajabi M, Solomon S, Poole A R. Hormonal regulation of interstitial collagenase in the uterine cervix of the pregnant Guinea pig. Endocrinology 1990;128:863–871.
28. Huang H Y, Wen Y, Irwin J C, Kruessel J S, Soong Y K, Polan M L. Cytokine-mediated regulation of 92-kilodalton Type IV collagenase, tissue inhibitor of metalloproteinase-1 (TIMP-1), and TIMP-3 messenger ribonucleic acid expression in human endometrial stromal cells. J Clin Endocrinol Metab 1998;83: 1721–1729.
29. Bhatia N N, Bergman A, Karram M M. Effects of estrogen on urethral function in women with urinary incontinence. Am J Obstet Gynecol 1989;160–176–181.
30. Fantl J A, Wyman J F, Anderson R L, Matt D W, Bump R C. Postmenopausal urinary incontinence: comparison between non-estrogen-supplemented and estrogen-supplemented women. Obstet Gynecol 1988;71:823–828.
31. Sato T, Ito A, Mori Y, Yamashita K, Hayakawa T, Nagase H. Hormonal regulation of collagenolysis in uterine cervical fibroblasts. Modulation of synthesis of procollagenase, prostromeylsin and tissue inhibitor of metalloproteinases (TIMP) by progesterone and oestradiol-17 beta. Biochem J 1991;275:645–650.
32. Matrisian L M, Gaire M, Rodgers W H, Osteen K G. Metalloproteinase expression and hormonal regulation during tissue remodeling in the cycling human endometrium Koide H, Hayashi T (eds): Extracellular Matrix in the Kidney. Contrib Nephrol, Basel, Karger, 1994;107:94–100.
33. Mäkinen J, Kähäri V M, Söderström K O, Vuorio E, Hirvonen T. Collagen synthesis in the vaginal connective tissue of patients with and without uterine prolapse. Eur J Obstet Gynecol Reprod Biol 1987;24:319–325.
34. Smith P, Heimer G, Norgren A, Ulmsten U. Steroid hormone receptors in pelvic muscles and ligaments in women. Gynecol Obstet Invest 1990;30:27–30.
35. Mochizuki M, Honda T, Tojo S. Collagenolytic activity and steroid levels after administration of dehydroepiandrosterone sulfate. Int J Gynaecol Obstet 1978;16:248–253.
36. Bigatel D A, Elmore J R, Carey D J, Cizmeci-Smith G, Franklin D P, Youkey J R. The matrix metalloproteinase inhibitor BB-94 limits expansion of experimental abdominal aortic aneurysms. J Vasc Surg 1999;29:130–138.
37. Lombard M A, Wallace T L, Kubicek M F, Petzold G L, Mitchell M A, Hendges S K, Wilks J W. Synthetic matrix metalloproteinase inhibitors and tissue inhibitor of metalloproteinase (TIMP)-2, but not TIMP-1, inhibit shedding of tumor necrosis factor-α receptors in a human colon adenocarcinoma (Colo 205) cell line. Cancer Research 1998;58:4001–4007.
38. Wojtowicz-Praga S, Torri J, Johnson M, Steen V, Marshall J, Ness E, Dickson R, Sale M, Rasmussen H S, Chiodo T A, Hawkins M J. Phase I trial of Marimastat, a novel matrix metalloproteinase inhibitor, administered orally to patients with advanced lung cancer. J Clin Oncol 1998;16:2150–2156.
39. Moore G, Liao S, Curci J A, Starcher B C, Martin R L, Hendricks R T, Chen J J, Thompson R W. Suppression of experimental abdominal aortic aneurysms by systemic treatment with a hydroxamate-based matrix metalloproteinase inhibitor (RS 132908). J Vasc Surg 1999;29:522–532.
40. Abbruzzese T A, Guzman R J, Martin R L, Yee C, Zarins C K, Dalman R L. Matrix metalloproteinase inhibition limits arterial enlargement in a rodent arteriovenous fistula model. Surgery 1998;124:328–335.
41. Chen B H, Wen Y, Hao L, Smith K, Polan M L. Collagen metabolism and turnover in women with stress urinary incontinence. Abstract submitted for presentation to the 20th Annual Scientific Meeting of the American Urogynecologic Society, Oct. 14–16, 1999.
42. Uberla K, Platzer C, Diamantstein T, Blankenstein T. Generation of competitor DNA fragments for quantitative PCR. PCR Methods Appl 1991; 1: 136–139.
43. Diviacco S, Norio P, Zentilin L, Menso S, Clementi M, Biamonti G, Riva S, Falaschi A, Giacca M. A novel procedure for quantitative polymerase chain reaction by coamplification of competitive templates. Gene 1992;15: 122:313–320.
44. SouazéF, Ntodou-ThoméA, Tran C Y, Rostene W, Forgez P. Quantitative RT-PCR: limits and accuracy. BioTechniques 1996;21:280–285.
45. Nakada M, Nakamura H, Ikeda E, Fujimoto N, Yamashita J, Sato H, Seiki M, Okada Y. Expression and tissue localization of membrane-type 1, 2 and 3 matrix metalloproteinases in human astrocytic tumors. Am J Pathol 1999;154:417–428.
46. Malmström A, Fransson L-A, Hook M. Lindahl U. Biosynthesis of dermatan sulfate. Formation of L-iduronic acid residues. J Biol Chem 1975;250–3419–3425.
47. Ryan J N, Woessner J F Jr. Mammalian collagenase: direct demonstration in homogenates of involuting rat uterus. Biochem Biophys Res Commun 1971;44:144–149.
48. Eickelberg O, Sommerfeld C O, Wyser C, Tamm M, Reichenberger F, Bardin P G, Soler M, Roth M, Perruchoud A P. MMP and TIMP expression pattern in pleural effusions of different origins. Am J Respir Crit Care Med 1997; 156:1987–1992.
49. Uebelhart D, Gineyts E, Chapuy M, Delmas P. Urinary excretion of pyridinium crosslinks: a new marker of bone resorption in metabolic bone disease. Bone Miner 1990;8:87–96.
50. Huang H Y, Wen Y. Raga F, Kruessel J S, Soong Y K, Polan M L. Interleukin-1β (IL-1β) and transforming growth factor-β (TGF-β) mediated regulation of 92 kD type IV collagenase, tissue inhibitor of metalloproteinase-1 (TIMP-1) and tissue inhibitor of metalloproteinase-3 (TIMP-3) expression in human endometrial stromal cells. Fertil Steril, submitted.
51. Moll U M, Youngleib G L, Rosinski K B, Quihley J P. Tumor promoter-stimulated Mr 92,000 gelatinase secreted by normal and malignant human cells: isolation and characterization of the enzyme from HT1080 tumor cells. Cancer Res 1988;51:107–145.
52 Shea, L D, Smiley, E, Bonadio, J, Mooney, D J. DNA delivery from polymer matrices for tissue engineering. Nature Biotechnol. 1999; 17: 551–554.

What is claimed is:

1. A method for diagnosing urinary incontinence or predisposition to urinary incontinence in a subject comprising assessing the degree of proteolysis of collagen in pelvic supporting tissue of the subject.

2. The method of claim 1, wherein the degree of proteolysis is assessed by determining one or more MMP mRNA levels in pelvic supporting tissue of the subject; determining one or more TIMP mRNA levels in pelvic supporting tissue in the subject; calculating a ratio of MMP/TIMP mRNA levels; and comparing the ratio to a predetermined indicator of normal and abnormal values for the ratio.

3. The method of claim 2, wherein the ratio is based on determinations of MMP-1 and TIMP-1 levels in pelvic supporting tissue in the subject.

4. The method of claim 2, wherein the pelvic supporting tissue is selected from the group consisting of: vaginal cuff tissue; periurethral tissue; periuterine tissue; vaginal epithelium; and cultured cells from pelvic supporting tissue.

5. The method of claim 2, wherein the predetermined indicator is an empirically determined value.

6. The method of claim 2, wherein the predetermined indicator is a previously measured value of MMP/TIMP level in the subject.

7. The method of claim 2, further including determining collagenase activity in pelvic supporting tissue in the subject and comparing the activity to a predetermined indicator.

8. A kit for use with the method of claim 2, comprising a test for the level of one or more MMPs in a tissue sample, a test for the level of one or more TIMPs in a tissue sample, and a predetermined indicator of normal and abnormal values for the MMP/TIMP ratio.

9. A method for treating a patient diagnosed as having urinary incontinence or predisposition to urinary incontinence according to the method of claim 2, comprising reducing proteolysis of collagen in pelvic supporting tissue of the patient and determining the effect of the treatment on the patient's condition.

10. The method of claim 9, wherein reducing proteolysis of collagen in pelvic supporting tissue is accomplished by administering to the patient an effective amount of one or more of the following:
  (a) an MMP inhibitor;
  (b) a TIMP or a TIMP analog or derivative;
  (c) a modulator of MMP levels; and
  (d) a modulator of TIMP levels.

11. The method of claim 2, wherein the ratio is based on determinations of mRNA levels of one or more MMPs selected from the group consisting of MMP-1, MMP-2 and MMP-9 and one or more TIMPs selected from the group consisting of TIMP-1, TIMP-2 and TIMP-3.

12. The method of claim 1, wherein the degree of proteolysis is assessed by measuring collagenase activity in pelvic supporting tissue in the subject and comparing the activity to a predetermined indicator of normal and abnormal values.

* * * * *

SEQUENCE LISTING

<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Made in a lab

<400> SEQUENCE: 1
ttccacaggt cccacaaccg cagc                                          24

<210> SEQ ID NO 2
<211> LENGTH: 18
<212> TYPE: DNA
<213> ORGANISM: Artificial Sequence
<220> FEATURE:
<223> OTHER INFORMATION: Made in a lab

<400> SEQUENCE: 2
cgtccacaag caatgagt                                                 18

<210> SEQ ID NO 3
<211> LENGTH: 32
<212> TYPE: DNA
<213> ORGANISM: Artificial Sequence
<220> FEATURE:
<223> OTHER INFORMATION: Made in a lab

<400> SEQUENCE: 3
cgtccacaag caatgagtgg ctgttccagg ga                                 32

<210> SEQ ID NO 4
<211> LENGTH: 18
<212> TYPE: DNA
<213> ORGANISM: Artificial Sequence
<220> FEATURE:
<223> OTHER INFORMATION: Made in a lab

<400> SEQUENCE: 4
tgcagctgcc cggtgcac                                                 18

<210> SEQ ID NO 5
<211> LENGTH: 21
<212> TYPE: DNA
<213> ORGANISM: Artificial Sequence
<220> FEATURE:
<223> OTHER INFORMATION: Made in a lab

<400> SEQUENCE: 5
ttatgggtcc tcgatgtcga g                                             21

<210> SEQ ID NO 6
<211> LENGTH: 36
<212> TYPE: DNA
<213> ORGANISM: Artificial Sequence
<220> FEATURE:
<223> OTHER INFORMATION: Made in a lab

<400> SEQUENCE: 6
ttatgggtcc tcgatgtcga ggaggagggg gccgtg                             36

<210> SEQ ID NO 7
<211> LENGTH: 22

```
<212> TYPE: DNA
<213> ORGANISM: Artificial Sequence
<220> FEATURE:
<223> OTHER INFORMATION: Made in a lab

<400> SEQUENCE: 7
taccagaaag aatgaggaac ct                                             22

<210> SEQ ID NO 8
<211> LENGTH: 21
<212> TYPE: DNA
<213> ORGANISM: Artificial Sequence
<220> FEATURE:
<223> OTHER INFORMATION: Made in a lab

<400> SEQUENCE: 8
agagagggtg ctgacggtgt t                                              21

<210> SEQ ID NO 9
<211> LENGTH: 36
<212> TYPE: DNA
<213> ORGANISM: Artificial Sequence
<220> FEATURE:
<223> OTHER INFORMATION: Made in a lab

<400> SEQUENCE: 9
agagagggtg ctgacggtgt tcagactcag gaacat                              36

<210> SEQ ID NO 10
<211> LENGTH: 22
<212> TYPE: DNA
<213> ORGANISM: Artificial Sequence
<220> FEATURE:
<223> OTHER INFORMATION: Made in a lab

<400> SEQUENCE: 10
tcggccccaa agcagcagct tc                                             22

<210> SEQ ID NO 11
<211> LENGTH: 21
<212> TYPE: DNA
<213> ORGANISM: Artificial Sequence
<220> FEATURE:
<223> OTHER INFORMATION: Made in a lab

<400> SEQUENCE: 11
cttcatggtg tctgcatcag c                                              21

<210> SEQ ID NO 12
<211> LENGTH: 20
<212> TYPE: DNA
<213> ORGANISM: Artificial Sequence
<220> FEATURE:
<223> OTHER INFORMATION: Made in a lab

<400> SEQUENCE: 12
acctggatgc cgtcgtggac                                                20

<210> SEQ ID NO 13
<211> LENGTH: 20
<212> TYPE: DNA
<213> ORGANISM: Artificial Sequence
<220> FEATURE:
<223> OTHER INFORMATION: Made in a lab

<400> SEQUENCE: 13
```

```
tgtggcagca ccagggcagc                                                    20

<210> SEQ ID NO 14
<211> LENGTH: 35
<212> TYPE: DNA
<213> ORGANISM: Artificial Sequence
<220> FEATURE:
<223> OTHER INFORMATION: Made in a lab

<400> SEQUENCE: 14
tgtggcagca ccagggcagc gtgggagcca gggcc                                   35

<210> SEQ ID NO 15
<211> LENGTH: 21
<212> TYPE: DNA
<213> ORGANISM: Artificial Sequence
<220> FEATURE:
<223> OTHER INFORMATION: Made in a lab

<400> SEQUENCE: 15
gcctgccact tcccttcat c                                                   21

<210> SEQ ID NO 16
<211> LENGTH: 21
<212> TYPE: DNA
<213> ORGANISM: Artificial Sequence
<220> FEATURE:
<223> OTHER INFORMATION: Made in a lab

<400> SEQUENCE: 16
ccccacttct tgtcgctgtc a                                                  21

<210> SEQ ID NO 17
<211> LENGTH: 33
<212> TYPE: DNA
<213> ORGANISM: Artificial Sequence
<220> FEATURE:
<223> OTHER INFORMATION: Made in a lab

<400> SEQUENCE: 17
ccccacttct tgtcgctgtc agtttcccat cag                                     33
```